United States Patent [19]

Maget et al.

[11] Patent Number: 4,687,423
[45] Date of Patent: Aug. 18, 1987

[54] ELECTROCHEMICALLY-DRIVEN PULSATILE DRUG DISPENSER

[75] Inventors: Henri J. R. Maget, Los Altos; Paul Krejci, Pacific Beach, both of Calif.

[73] Assignee: Ivac Corporation, San Diego, Calif.

[21] Appl. No.: 742,192

[22] Filed: Jun. 7, 1985

[51] Int. Cl.⁴ ............................................. A61M 31/00
[52] U.S. Cl. ..................................... 417/379; 417/395
[58] Field of Search ......................... 417/48, 379, 395; 604/891, 892; 204/301

[56] References Cited

U.S. PATENT DOCUMENTS

| | | | |
|---|---|---|---|
| 1,963,993 | 6/1934 | Hendriks et al. | 417/395 |
| 2,370,068 | 2/1945 | Palm | 91/346 X |
| 2,766,907 | 10/1956 | Wallace, Jr. | 222/94 |
| 3,199,511 | 8/1965 | Kulick | 128/DIG. 12 |
| 3,460,482 | 8/1969 | Jackson | 417/395 X |
| 3,894,538 | 7/1975 | Richter | 204/301 X |
| 3,923,426 | 12/1975 | Theeuwes | 417/48 |
| 3,995,632 | 12/1976 | Nakono et al. | 604/892 |
| 4,034,756 | 7/1977 | Higuchi et al. | 604/892 |
| 4,237,881 | 12/1980 | Beigler et al. | 128/214 |
| 4,272,329 | 6/1981 | Hetrick et al. | 204/425 X |
| 4,300,552 | 11/1981 | Cannon | 128/214 |
| 4,332,246 | 6/1982 | Thomson | 128/DIG. 12 |
| 4,345,594 | 8/1982 | Bisera et al. | 128/DIG. 12 |
| 4,402,817 | 9/1983 | Maget | 204/301 |
| 4,430,078 | 2/1984 | Sprague | 128/DIG. 12 |
| 4,439,196 | 3/1984 | Higuchi | 604/890 |
| 4,447,224 | 5/1984 | DeCant et al. | 128/DIG. 12 |
| 4,498,968 | 2/1985 | Yamada et al. | 204/425 X |
| 4,552,698 | 6/1985 | Maget | 204/301 |

FOREIGN PATENT DOCUMENTS 2029506 8/1979 United Kingdom .

Primary Examiner—Leonard E. Smith
Attorney, Agent, or Firm—Fulwider Patton Rieber Lee & Utecht

[57] ABSTRACT

An improved drug dispenser for the pulsatile or peristaltic delivery of drugs. The drug dispenser includes a fluid reservoir for storing the drug to be dispensed, an electrochemical pump for pumping the drug from the fluid reservoir, and a pump valve responsive to the pump pressure such that when the pump pressure reaches some predetermined value, the pump valve releases the pressure exerted upon the drug. The result is a low cost, low weight ad efficient drug dispenser for the pulsatile delivery of drugs.

15 Claims, 3 Drawing Figures

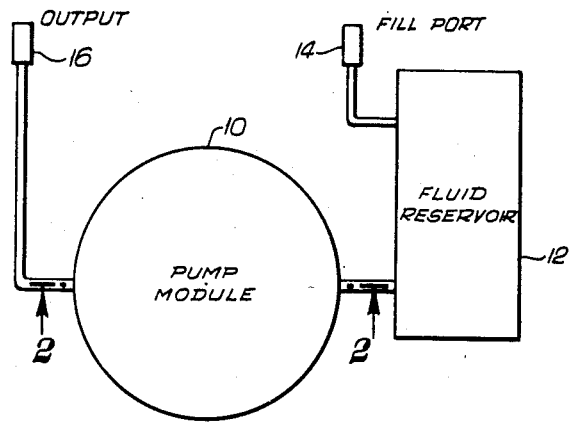
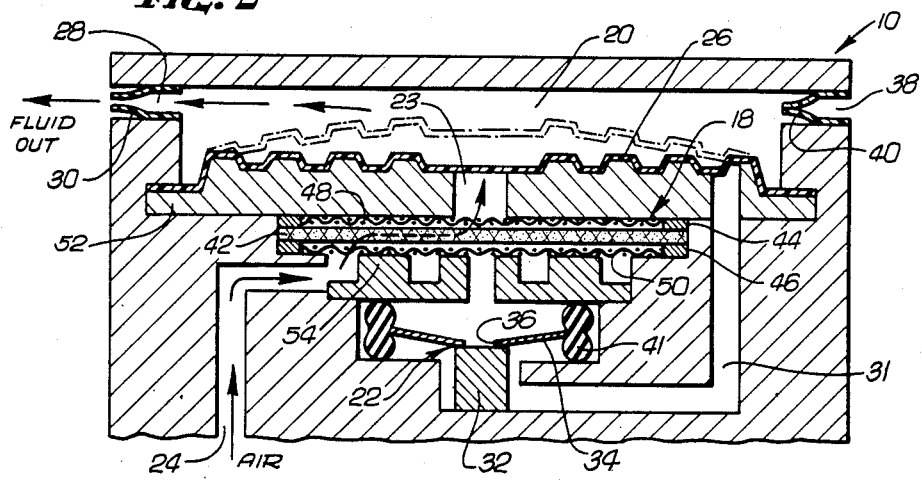
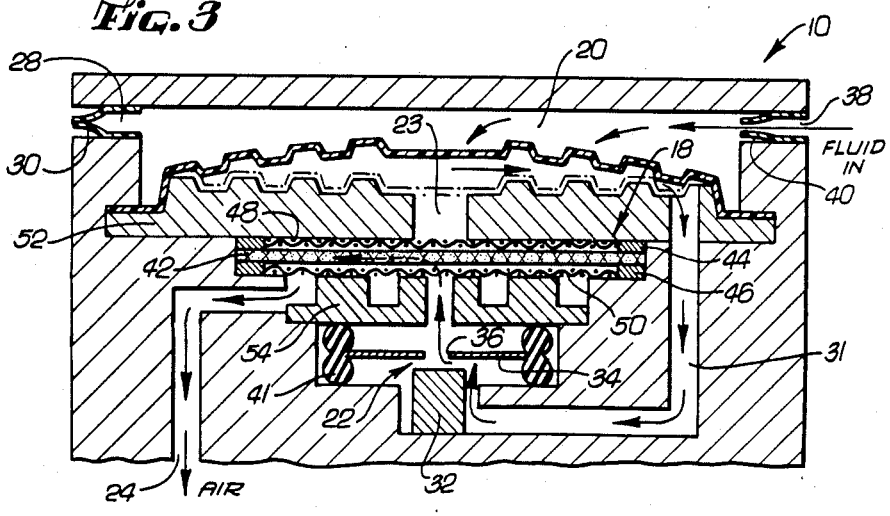

ELECTROCHEMICALLY-DRIVEN PULSATILE DRUG DISPENSER

BACKGROUND OF THE INVENTION

This invention relates generally to drug infusion devices and, more particularly, to drug infusion devices driven by electrochemical pumps.

A variety of types of drug infusion devices are used to dispense drugs to a patient continuously over a period of many hours. Such devices include gravity dispensers, mechanical pump dispensers, pressurized gas dispensers and osmotic pressure dispensers. A gravity dispenser utilizes the force of gravity to dispense a drug from the familiar plasma bottle suspended above the patient. A mechanical pump dispenser generally includes some type of electrically-driven mechanical pump, while a pressurized gas dispenser utilizes a tank of some suitable pressurized gas to dispense the drug. An osmotic pressure dispenser relies on a solute that exhibits an osmotic pressure gradient against water to dispense the drug.

However, when small quantities of drugs, such as hormones, must be administered continuously over a period of many hours, a drug dispenser that is highly accurate, yet small enough to be portable, that can be miniaturized and therefore implanted, and that has no moving parts is preferred. None of the above-mentioned types of drug dispensers can meet all of these requirements. A copending patent application filed by one of the present joint inventors, entitled ELECTROCHEMICALLY DRIVEN DRUG DISPENSER, Ser. No. 729,860, discloses an electrochemically driven drug dispenser that does meet all of these requirements. The electrochemically driven drug dispenser includes an electrochemical pump that operates as a variable pressure source and provides highly accurate control of the delivery rate of these small quantities of drugs.

Although the electrochemically driven drug dispenser disclosed in the above-mentioned patent application has many advantages, it operates in a constant delivery mode and is not easily adapted to deliver drugs in a pulsatile or peristaltic delivery mode. Pulsatile or peristaltic drug delivery duplicates the body's natural delivery of, for example, certain types of hormones. Accordingly, there has been a need for a drug dispenser which is portable, can be miniaturized and therefore implanted, is highly accurate in the delivery of small quantities of drugs, and can deliver drugs with a pulsatile or peristaltic motion.

SUMMARY OF THE INVENTION

The present invention resides in an electrochemically driven drug dispenser for the pulsatile or peristaltic delivery of drugs. The drug dispenser includes a fluid reservoir for storing the drug to be dispensed, an electrochemical pump for pumping the drug from the fluid reservoir, and a pump valve responsive to the pump pressure such that when the pump pressure reaches some predetermined value, the pump valve releases the pressure exerted upon the drug.

More specifically, the fluid reservoir contains a collapsible bag for storing the drug to be dispensed. The reservoir can be refilled via a fill port. The electrochemical pump includes an electrochemical cell, comprised of an electrolytic membrane and an electrode disposed on either side of the membrane, and a pump chamber. Applying a voltage across the electrodes causes oxygen to be extracted from the air and driven across the membrane. The pressurized oxygen moves a diaphragm, disposed between the electrochemical cell and the pump chamber, upward into the pump chamber, thereby expelling the drug in the pump chamber out of the chamber via an outlet port. When the pressure of the oxygen reaches a predetermined value, the pump valve releases the oxygen and allows the diaphragm to move back to its rest position, thereby refilling the pump chamber with the drug from the fluid reservoir. The pump is then ready for the next cycle.

It will be appreciated from the foregoing that the present invention provides a low cost, low weight and efficient drug dispenser and represents a significant advance in drug delivery dispensers. Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 1 is an elevational view of an electrochemically driven drug dispenser for the pulsatile delivery of drugs;

FIG. 2 is an enlarged sectional view of an electrochemical pump and a pump valve, illustrating the pump stroke; and FIG. 3 is an enlarged sectional view of the electrochemical pump and the pump valve, illustrating the intake stroke.

DESCRIPTION OF THE PREFERRED EMBODIMENT

As shown in the drawings for purposes of illustration, the present invention is embodied in a novel drug dispensing device. Highly accurate and miniature drug dispensing devices are required for administering small quantities of drugs, such as hormones, continuously over a period of many hours.

These requirements have been met with an electrochemically driven drug dispenser. However, such a dispenser is not easily adapted to deliver drugs in a pulsatile or peristaltic motion.

In accordance with the present invention, an electrochemically-driven pulsatile drug dispenser includes a fluid reservoir for storing the drug to be dispensed, an electrochemical pump for pumping the drug from the fluid reservoir, and a pump valve responsive to the pump pressure such that when the pump pressure reaches some predetermined value, the pump valve releases the pressure exerted upon the drug.

FIG. 1 illustrates a preferred embodiment of the electrochemically-driven drug dispenser. The drug dispenser comprises a pump module 10 and a fluid resevoir 12. The fluid reservoir 12 is filled with a drug via a fill port 14. The pump module 10 pumps the drug stored in the fluid reservoir 12 to the patient via an output line 16.

FIGS. 2 and 3 illustrate in detail the pump module 10. FIG. 2 shows the pump stoke of the pump module 10, in which the drug is expelled from the pump module 10 via the output line 16. FIG. 3 shows the intake stroke of the pump module 10, in which the pump module 10 is refilled from the fluid reservoir 12.

The pump module 10 includes an electrochemical cell 18, a pump chamber 20 and a pump valve 22. The electrochemical cell 18 pumps oxygen into the pump chamber 20 via a diaphragm conduit 23. The electrochemical cell 18 extracts the oxygen from the air via an air intake port 24. The oxygen is pumped across the electrochemical cell 18 creating a gas pressure under a flexible and expansible diaphragm 26, disposed between the electrochemical cell 18 and the pump chamber 20. The diaphragm 26 expands into the pump chamber 20 and squeezes the drug contained in the pump chamber out an outlet port 28. The outlet port 28 includes a check valve 30 to prevent flow of the drug back into the pump chamber 20.

During the pump stroke, in which the oxygen expands the diaphragm 26 into the pump chamber 20, the pressurized oxygen is likewise transmitted to the pump valve 22 through a pump valve conduit 31. The pump valve 22 includes a pump valve seat 32 and a pump valve diaphragm 34. When the pressure of the oxygen has reached a predetermined value, the pump valve diaphragm 34 moves upward away from the pump valve seat 32. This allows the oxygen to flow through a perforation 36 in the pump valve diaphragm 34 to the inlet side of the electrochemical cell 18. The oxygen pressure under the diaphragm 26 is thereby reduced, allowing the diaphragm 26 to return to its rest position. The retraction of the diaphragm 26 refills the pump chamber 20 with the drug stored in the fluid reservoir 12 through an inlet port 38. The inlet port 38 includes a check valve 40 to prevent flow of the drug back into the fluid reservoir 12.

The pump valve diaphragm 34 is centered between two O-rings 41 and is constructed of a material such that the oxygen pressure required to move the diaphragm 34 off the pump valve seat 32 can be preselected by the proper selection of type and thickness of material. After the pump valve diaphragm 34 releases the oxygen pressure, it snaps back to its rest position. The time requried for the diaphragm 34 to snap back to its rest position is dependent on the time requried to release the oxygen pressure, which is dependent on the diameter of the perforation 36. Consequently, the timing of the refill and pump strokes, and, therefore, the timing of the pulsatile motion, can be preselected and be on the order of a few seconds to a few milliseconds, which is essentially continuous delivery.

The electrochemical cell 18 is comprised of an electrolytic membrane 42 and a pair of conductive electrodes 44 and 46 and a pair of screen elements 48 and 50 disposed on opposite surfaces of the electrolytic membrane 42. The screen elements 48 and 50 act as current collectors and also allow for the travel of oxygen to conduit 23 and intake port 24. The electrochemical cell 18 is supported by a pair of electrode supports 52 and 54. Electrode support 52 also provides a support for the diaphragm 26 while in the diaphragm's rest position.

The present invention provides a low cost and low weight electrochemically driven drug dispenser for the pulsatile or peristaltic delivery of drugs. Furthermore, the dispenser operates very efficiently, therefore requiring little power for operation, because almost pure oxygen is recycled from under the diaphragm through the conduit to the inlet side of the electrochemical cell. The system operates nearly as a closed loop except for some losses due to oxygen flow back through the air intake port. Or, if the pump is filled initially with pure oxygen, the air intake port can be closed off and the drug dispenser can then be implanted.

From the foregoing, it will be appreciated that the present electrochemically driven drug dispenser provides a very efficient, low cost and low weight drug dispenser for the pulsatile or peristaltic delivery of drugs. Although several embodiments of the invention have been shown and described, it will be apparent that other adaptations and modifications can be made without departing from the spirit and scope of the invention.

We claim:

1. An electrochemically-driven pulsatile drug dispenser, comprising:
   a pump chamber having a pump inlet and a pump outlet;
   an electrochemical pump for pumping a motive fluid, said electrochemical pump having a motive fluid inlet and a motive fluid outlet;
   pressure transmission means disposed between said pump chamber and said motive fluid outlet, said pressure transmission means being displaced in response to pressure of said motive fluid at said motive fluid outlet; and
   a pump valve having a valve inlet in fluid communication with said motive fluid outlet and a valve outlet in fluid communication with said motive fluid inlet, said pump valve being responsive to said motive fluid pressure whereby said pump valve releases said motive fluid pressure exerted upon said pressure transmission means when said motive fluid pressure reaches a predetermined value, wherein the pump valve includes:
   a pump valve seat; and
   a pump valve diaphragm having a perforation, wherein the pump valve diaphragm moves upward from the pump valve seat and, at the predetermined value, snaps open and releases the pump pressure through the perforation.

2. The electrochemically-driven pulsatile drug dispenser as defined in claim 1, and further comprising:
   a reservoir for storing the drug.

3. The electrochemically-driven pulsatile drug dispenser as defined in claim 2, wherein the electrochemical pump includes:
   an electrochemical cell for pressurizing a gas as said motive fluid.

4. The electrochemically-driven pulsatile drug dispenser as defined in claim 3, wherein the electrochemical cell includes:
   an electrolytic membrane; and
   a pair of electrodes disposed on either side of the electrolytic membrane.

5. The electrochemically-driven pulsatile drug dispenser as defined in claim 3, wherein said pressure transmission means comprises:
   a flexible diaphragm for exerting the gas pressure on a drug in the pump chamber.

6. A pulsatile drug dispenser, comprising:
   a pump chamber for containing a drug, said pump chamber having a pump inlet and a pump outlet;
   means for pressurizing a motive fluid, said means having a motive fluid inlet and a motive fluid outlet;
   pressure transmission means disposed between said pump chamber and said motive fluid outlet, said pressure transmission means being displaced in response to pressure of said motive fluid at said motive fluid outlet for pumping said drug from said pump chamber;
   pressure responsive means having an inlet in fluid communication with said motive fluid outlet and an outlet in fluid communication with said motive fluid inlet, said pressure responsive means being responsive to said motive fluid pressure whereby said pressure responsive means releases said motive fluid pressure exerted upon said pressure transmission means when said motive fluid pressure reaches a predetermine value, thereby pumping said drug in a pulsatile or peristaltic motion, wherein the pressure responsive means includes:

a pump valve seat; and a pump valve diaphragm having a perforation, wherein the pump valve diaphragm moves upward from the pump valve seat and, at the predetermined value, snaps open and releases the fluid through the perforation.

7. The pulsatile drug dispenser as defined in a claim 6, and further comprising:

means for storing the drug.

8. The pulsatile drug dispenser as defined in claim 6, wherein the means for pressurizing a motive fluid includes:

an electrochemical cell for pressurizing the fluid.

9. The pulsatile drug dispenser as defined in claim 8, wherein the electrochemical cell includes:

an electrolytic membrane; and a pair of electrodes disposed on either side of the electrolytic membrane.

10. The pulsatile drug dispenser as defined in claim 8, wherein said pressure transmission means comprises:

a flexible diaphragm for exerting the motive fluid pressure on the drug in the pump chamber.

11. An electrochemically drive pulsatile drug dispenser, comprising:

a housing;

a pump chamber disposed in said housing and having a pump inlet and a pump outlet;

an electrochemical pump disposed in said housing for pumping a gaseous motive fluid, said electrochemical pump having a motive fluid inlet and a motive fluid outlet;

pressure transmission means disposed in said housing between said pump chamber and said motive fluid outlet, said pressure transmission means being displaced in response to pressure of said motive fluid at said motive fluid outlet;

a pump valve having a valve inlet and having a valve outlet in fluid communication with said motive fluid inlet; and a fluid conduit in said housing having an outlet end in fluid communication with said valve inlet and having an inlet end in fluid communication with said motive fluid exerting pressure upon said pressure transmission means, said inlet end being isolated from said motive fluid outlet, whereby said pump valve is responsive to said motive fluid pressure and releases said motive fluid pressure exerted upon said pressure transmission means when said motive fluid pressure reaches a predetermined value.

12. The electrochemically-driven pulsatile drug dispenser as defined in claim 11, wherein the pump valve comprises:

a pump valve seat; and a pump valve diaphragm having a perforation, wherein the pump valve diaphragm moves upward from the pump valve seat and, at the predetermined value, snaps open and releases the pump pressure through the perforation.

13. The electrochemically-driven pulsatile drug dispenser as defined in claim 11, wherein said pressure transmission means comprises a flexible diaphragm for exerting said motive fluid pressure on a drug in said pump chamber.

14. The electrochemically-driven pulsatile drug dispenser as defined in claim 13, wherein the gaseous motive fluid comprises air.

15. The electrochemically-driven pulsatile drug dispenser as defined in claim 14, further comprising an air conduit in said housing establishing communication between said motive fluid inlet and ambient atmosphere, whereby said motive fluid comprises air from said ambient atmosphere.

* * * * *